United States Patent
Lim et al.

(10) Patent No.: US 8,583,225 B2
(45) Date of Patent: Nov. 12, 2013

(54) SYSTEM AND METHOD FOR DETECTING SKIN PENETRATION

(75) Inventors: Chee Yen Lim, Singapore (SG); Szu Cheng Lai, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 479 days.

(21) Appl. No.: 12/675,031

(22) PCT Filed: Aug. 24, 2007

(86) PCT No.: PCT/SG2007/000279
§ 371 (c)(1), (2), (4) Date: Jan. 17, 2011

(87) PCT Pub. No.: WO2009/029044
PCT Pub. Date: Mar. 5, 2009

(65) Prior Publication Data
US 2011/0105942 A1    May 5, 2011

(51) Int. Cl.
A61B 5/053    (2006.01)

(52) U.S. Cl.
USPC .......................................... 600/547; 600/587

(58) Field of Classification Search
USPC .................. 600/547, 583, 587; 606/181, 183
See application file for complete search history.

(56) References Cited

U.S. PATENT DOCUMENTS

| | | | |
|---|---|---|---|
| 2,763,935 A * | 9/1956 | Whaley et al. .................. 33/511 |
| 3,085,566 A * | 4/1963 | Tolles ........................... 600/547 |
| 3,957,036 A * | 5/1976 | Normann ....................... 600/377 |
| 4,016,886 A * | 4/1977 | Doss et al. ...................... 607/99 |
| 4,690,152 A | 9/1987 | Juncosa |
| 5,271,413 A | 12/1993 | Dalamagas et al. |
| 5,454,377 A * | 10/1995 | Dzwonczyk et al. ......... 600/547 |
| 6,337,994 B1 | 1/2002 | Stoianovici et al. |
| 7,198,606 B2 * | 4/2007 | Boecker et al. ............... 600/583 |
| 7,645,263 B2 * | 1/2010 | Angel et al. ................... 604/116 |
| 2002/0010414 A1 | 1/2002 | Coston et al. |
| 2002/0042594 A1 * | 4/2002 | Lum et al. ..................... 604/117 |
| 2003/0083641 A1 | 5/2003 | Angel et al. |
| 2004/0249310 A1 * | 12/2004 | Shartle et al. ................. 600/583 |
| 2006/0025765 A1 * | 2/2006 | Landman et al. ............... 606/48 |

(Continued)

FOREIGN PATENT DOCUMENTS

| | | |
|---|---|---|
| EP | 1757227 A2 | 2/2007 |
| GB | 2335990 A | 10/1999 |

(Continued)

OTHER PUBLICATIONS

First Office Action in JP Patent Application No. 2010-521819, English translation included, Mar. 18, 2013.

*Primary Examiner* — Sean Dougherty
*Assistant Examiner* — Michael C Stout
(74) *Attorney, Agent, or Firm* — Thomas A. Runk; Fulwider Patton LLP

(57) ABSTRACT

A system and method for detecting skin penetration. The system comprises an invasive component for penetrating the skin; a dummy electrode for making contact with the surface of the skin; at least one penetrating electrode disposed in the invasive component; and a Wheatstone bridge circuit; wherein a resistance across the dummy electrode and the penetrating electrode constitutes one of the resistive legs of the Wheatstone bridge circuit and skin penetration of the invasive component is detected based on a differential output voltage from the Wheatstone bridge circuit.

29 Claims, 11 Drawing Sheets

(56) References Cited

U.S. PATENT DOCUMENTS

| | | | |
|---|---|---|---|
| 2006/0276724 A1* | 12/2006 | Freeman et al. | 600/583 |
| 2007/0129650 A1* | 6/2007 | Freeman et al. | 600/583 |
| 2007/0173740 A1* | 7/2007 | Chan et al. | 600/583 |
| 2008/0108910 A1* | 5/2008 | Hein et al. | 600/583 |
| 2008/0262379 A1* | 10/2008 | Gerber et al. | 600/549 |
| 2009/0036794 A1* | 2/2009 | Stubhaug et al. | 600/547 |

FOREIGN PATENT DOCUMENTS

| | | |
|---|---|---|
| JP | 63-143038 A | 6/1988 |
| JP | 63-283626 A | 11/1988 |
| JP | 7-303618 A | 11/1995 |
| JP | 2005-525150 A | 8/2005 |
| JP | 2006-520251 A | 9/2006 |
| JP | 2007-203039 A | 8/2007 |
| JP | 2008-534192 A | 8/2008 |
| WO | 96/14026 A1 | 5/1996 |
| WO | 2004/080306 A1 | 9/2004 |
| WO | 2005/044364 A1 | 5/2005 |
| WO | 2005/087305 A1 | 9/2005 |
| WO | 2006/057619 A1 | 6/2006 |
| WO | WO 2006105968 A1 * | 10/2006 ............... A61B 5/14 |
| WO | WO 2007075091 A2 * | 7/2007 ............. A61B 5/053 |
| WO | 2008/027011 A1 | 3/2008 |
| WO | 2008/036043 A1 | 3/2008 |

* cited by examiner

SYSTEM AND METHOD FOR DETECTING SKIN PENETRATION

CROSS-REFERENCE TO RELATED APPLICATIONS

This application is a U.S. National Phase of International Patent Application number PCT/SG2007/000279, filed 24 Aug. 2007, the entire contents of which are incorporated herein by reference.

FIELD OF INVENTION

The present invention relates broadly to a system and method for detecting skin penetration.

BACKGROUND

Skin penetration is a common procedure in various biomedical applications, particularly in minimally invasive drug delivery (via microneedles) where instant detection and/or great precision of skin penetration is desired. The ability to penetrate the skin reproducibly to a precise depth enables drugs to be delivered to the desired layers, which is currently the state of the art in transdermal drug delivery (i.e. delivering drug across and into the skin).

Other applications requiring precise control of skin penetration is body interstitial fluid extraction, e.g. blood sampling for blood content analysis. Blood sampling involves pricking a body site such as the finger tip or forearm to obtain a small amount of blood. The amount of blood is directly related to the wound created by a lancet. Since blood testing technology requires less and less blood for accurate testing, there exists a need to precisely control the penetration depth as it is also directly related to the trauma incurred. The deeper the penetration, the more traumatic and painful it is.

Lancets are small pointed needles used in pricking the body site to obtain small amount of blood for testing or blood sampling in general. Stainless steel lancets are currently used due to its strength and ease of maintenance. For a typical manufacturing process, a stainless steel wire needs to be cut into correct length and then ground to the desired sharpness. The cut and ground wire is then inserted into a mold set for injection molding a plastic component for safety containment and handling. There are several inherent problems associated with the prior art.

Stainless steel lancets are stiff and hard, and this is a potential risk of injury during the handling or disposal of these lancets. As the lancets are to be destroyed after use, there is a risk of infection. Stainless steel has very high melting temperature (1,420° C.), making the incineration process of used lancets very inconvenient for hospitals. There is a need to have lancets that can be functionally disabled after use. There is also an urgent solution required for the incineration or recycling of these bio-hazardous disposables.

Currently, the blood sampling process involves pricking a body site with a stainless steel lancet and collecting the blood sample using a test media such as a plastic test strip. It would be advantageous if the lancet, apart from pricking a body site, can also be used to collect or store the blood sample and/or then transport it to a location accessible for testing means. However, stainless steel having high strength and stiffness is not as suitable a candidate as polymers for incorporating these features on the lancet.

As an alternative, lancets are also made of plastic. However, these plastic lancets merely consist of solid tip for pricking or a channel for transporting the blood. There are still unsolved problems associated with these plastic lancets. Most plastic lancets with transport channel remains in the body for body fluid extraction. This procedure also contributes to an increased traumatic experience.

Most existing lancets are unable to perform sensing functions, such as detecting skin penetration or sensing the depth of penetration. The ability to control the depth of penetration allows pain to be managed effectively, and it also allows confirmation that a desired depth for drug delivery is achieved.

On the other hand, there have been several recent proposals to provide for measurements of penetration depth in lancets. However, in most of the proposed techniques, the depth of penetration is derived from the measurement of the absolute electrical characteristics of the skin, which involves correlation of measurements and calibration of equipment. This is imprecise and impractical for transdermal drug delivery.

The electrical properties of skin, change according to environmental and physiological factors and differ greatly from person to person and bodily regions. Most of the abovementioned proposals merely measure the absolute values of these properties directly, requiring too many precedent correlations before use, which can be impractical. For example, those described by US 2002/0042594 entitled "Apparatus and method for penetration with shaft having a sensor for sensing penetration depth" and US 2002/0010414 entitled "Tissue electroperforation for enhanced drug delivery and diagnostic sampling" do not address the wide variance of the impedance of the skin due to physiological and environmental factors. Although WO 2004/080306 entitled "System and method for piercing dermal tissue" attempts to address this issue, by averaging absolute values measured with multiple reference electrodes so as to alleviate the variance in skin impedance due to humidity, it fails in that it is dependent on many correlations having to be performed prior to actual use.

A need therefore exists to provide a system and method for detecting and measuring the depth of skin penetration that seeks to address at least one of the abovementioned problems.

SUMMARY

In accordance with a first aspect of the present invention there is provided a system for detecting skin penetration, the system comprising an invasive component for penetrating the skin; a dummy electrode for making contact with the surface of the skin; at least one penetrating electrode disposed in the invasive component; and a Wheatstone bridge circuit; wherein a resistance across the dummy electrode and the penetrating electrode constitutes one of the resistive legs of the Wheatstone bridge circuit and skin penetration of the invasive component is detected based on a differential output voltage from the Wheatstone bridge circuit.

The system may further comprise a first pair of reference electrodes for making contact with the surface of the skin, wherein a resistance across the first pair of reference electrodes constitutes the mirroring resistive leg, with respect to ground, of the Wheatstone bridge circuit.

One of the reference electrodes may be the dummy electrode.

The system may further comprise second and third pairs of reference electrode, each for making contact with the surface of the skin, wherein respective resistances across the second and third pairs of reference electrodes constitute the remaining resistive legs of the Wheatstone bridge circuit respectively.

A plurality of penetrating electrodes may be disposed in the invasive component.

Resistances across the dummy electrode and the respective penetrating electrodes may be multiplexed across one of the resistive legs of the Wheatstone and a penetration depth of the invasive component is detected based on differential output voltages from the Wheatstone bridge circuit for the respective resistances across the dummy electrode and the respective penetrating electrodes.

The invasive component may comprise a microneedle disposed in a lancing device, and the dummy electrode for making contact with the surface of the skin is disposed on a skin-contact face of the lancing device.

The invasive component may comprise a microneedle disposed in a lancing device, and the dummy electrode for making contact with the surface of the skin and the first pair of reference electrodes are disposed on a skin-contact face of the lancing device.

The invasive component may comprise a microneedle disposed in a lancing device, and the dummy electrode for making contact with the surface of the skin and the first, second, and third pairs of reference electrodes are disposed on a skin-contact face of the lancing device.

The invasive component may comprise a hollow or solid microneedle.

The invasive component may comprise a conductive microneedle.

The invasive component may comprise a non-conductive microneedle.

The invasive component may comprises a plastic microneedle.

The system may further comprise means for indicating skin penetration of the invasive component based on the differential output voltage from the Wheatstone bridge circuit.

The system as claimed in any one of the preceding claims, further comprising means for displaying the penetration depth of the invasive component based on the differential output voltages from the Wheatstone bridge circuit.

The reference and/or dummy electrodes may be disposed around an opening of a distal end of the lancing device.

In accordance with a second aspect of the present invention there is provided a method for detecting skin penetration, the method comprising the steps of penetrating the skin with an invasive component wherein at least one penetrating electrode is disposed in the invasive component; making contact between a dummy electrode and the surface of the skin; applying a resistance across the dummy electrode and the penetrating electrode as one of the resistive legs of a Wheatstone bridge circuit and; detecting skin penetration of the invasive component is detected based on a differential output voltage from the Wheatstone bridge circuit.

The method may further comprise the steps of making contact with the surface of the skin with a first pair of reference electrodes; and applying a resistance across the first pair of reference electrodes as the mirroring resistive leg, with respect to ground, of the Wheatstone bridge circuit.

One of the reference electrodes is the dummy electrode.

The method may further comprise the steps of making contact with the surface of the skin with second and third pairs of reference electrode, and applying respective resistances across the second and third pairs of reference electrodes as the remaining resistive legs of the Wheatstone bridge circuit respectively.

A plurality of penetrating electrodes may be disposed in the invasive component.

Resistances across the dummy electrode and the respective penetrating electrodes may be multiplexed across one of the resistive legs of the Wheatstone and a penetration depth of the invasive component is detected based on differential output voltages from the Wheatstone bridge circuit for the respective resistances across the dummy electrode and the respective penetrating electrodes.

The invasive component may comprise a microneedle disposed in a lancing device, and the dummy electrode for making contact with the surface of the skin is disposed on a skin-contact face of the lancing device.

The invasive component may comprise a microneedle disposed in a lancing device, and the dummy electrode for making contact with the surface of the skin and the first pair of reference electrodes are disposed on a skin-contact face of the lancing device.

The invasive component may comprise a microneedle disposed in a lancing device, and the dummy electrode for making contact with the surface of the skin and the first, second, and third pairs of reference electrodes are disposed on a skin-contact face of the lancing device.

The invasive component may comprise a hollow or solid microneedle.

The invasive component may comprise a conductive microneedle.

The invasive component may comprise a non-conductive microneedle.

The invasive component may comprise a plastic microneedle.

The method may further comprise the step of indicating skin penetration of the invasive component based on the differential output voltage from the Wheatstone bridge circuit.

The method may further comprise the step of displaying the penetration depth of the invasive component based on the differential output voltages from the Wheatstone bridge circuit.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
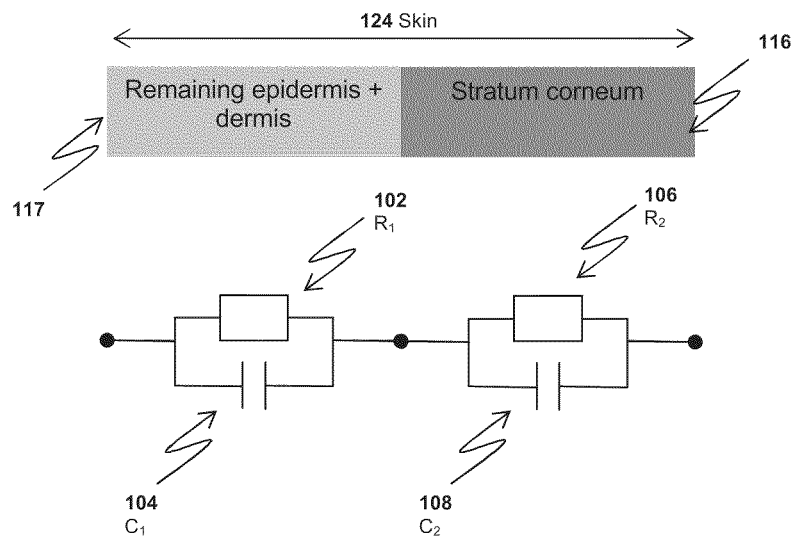
FIG. 1 shows a circuit model for representing the skin impedance.

The described embodiments seek to provide precise control of the depth of skin penetration of an invasive component for delivering a prescribed drug into a body. There are many instances that require precise skin penetration. The skin is the largest organ in our body. The skin serves as a protective barrier that insulates our bodies from hostile environment. The skin also helps to maintain body temperature for the body to function well. The body gathers sensory information from the environment through the skin. The body also derives its immunity from disease through the skin.

There are three layers of skin, namely epidermis, dermis and subcutaneous tissue. The epidermis is the outer layer of skin having thickness of roughly 0.05 mm to 1.50 mm. The epidermis is a good target for vaccine delivery because it contains antigen-presenting cells (APCs) and is immunocompetent (i.e. after picking up antigens, Langerhans cells migrate and move to the draining lymph nodes). However, such transdermal or epidermal vaccination strategy via the epidermis relies mainly on the ability to precisely deliver the vaccine to the desired layer. This remains a major challenge in epidermal vaccination due to the thinness of the epidermis.

The outermost sublayer, stratum corneum, is made of dead, flat skin cells that form an effective insulating layer to protect our body. However, for the purpose of transdermal drug delivery, it is important to breach the stratum corneum to effectively transport the drugs into the skin. This poses a great challenge to epidermal vaccination.

The dermis is on average 0.3 mm to 3.0 mm in thickness and contains the two sublayers: the papillary and reticular sublayers. The papillary dermis, which is next to epidermis, contains high degree of vascularity network to support the epidermis (which contains very few capillaries) with vital nutrients and also to regulate the temperature of the body by increasing or decreasing the blood flow in the capillary. Papillary dermis also contains the free sensory nerve endings. This is a good delivery site for drug delivery that requires systemic circulation.

The subcutaneous tissue is a layer of fat and connective tissue that houses larger blood vessels and nerves. This layer is important is the regulation of temperature of the skin itself and the body. The size of this layer varies throughout the body and from person to person.

Research has shown that delivering vaccine to the epidermal layer (i.e. second layer after stratum corneum) is more responsive and may require less quantity. Currently, there is no system that is able to ensure vaccine delivery to epidermis with satisfied reproducibility and precision.

Transdermal drug delivery has been recognised for more than 20 years but is still limited to drugs that have small molecular size (e.g. <1,000 Daltons). There are various penetration enhancers to extend these applications to wider drugs, including chemical and electrical (e.g. iontophoresis, electroosmosis, sonophoresis, etc.) means. Microneedles arise as an effective minimally invasive means to enhance transdermal drug delivery by breaching the stratum corneum. Notable successes have been reported, but there is still a fundamental issue in relation to wide acceptance of microneedles, due to the consistency and reproducibility of skin penetration by these tiny needles.

Most of the time, a needle or lancet is inserted into a body to extract body fluids or for blood testing. More than often, these invasive components are inserted more than required to ensure successful extraction, thereby incurring unnecessary trauma. Moreover, most lancing devices in the market do not provide visual access to the lancing site; the user will not know if there is any or enough skin penetration without removing the device from the site. Embodiments of the present invention can be tailored to detect and measure momentary skin penetration.

Figure 2:
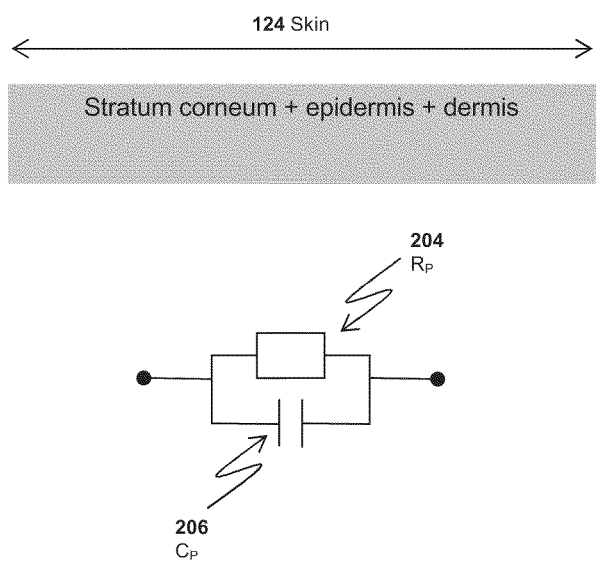
FIG. 2 shows a simplified circuit model for representing the skin impedance.

The impedance of the skin (i.e. the stratum corneum, the epidermis and the dermis) can be represented with equivalent circuit models comprising of capacitors and resistors for electrical analysis. The circuit model as shown in FIG. 1 illustrates that the human skin 124 forms a RC (i.e. resistive-capacitive) network where $R_1$ 102 and $C_1$ 104 represent the combined impedance due to the epidermis and dermis 117. $R_2$ 106 and $C_2$ 108 represent the impedance due to the stratum corneum 116. $R_1$ 102, $R_2$ 106 $C_1$ 104 and $C_2$ 108 as shown in FIG. 1 can be further simplified as $R_P$ 202 and $C_P$ 204 as shown in FIG. 2. Of valuable note is that the impedance of the stratum corneum in particular, dominates the overall skin impedance.

Embodiments of the present invention attempt to accurately detect skin penetration and the depth of penetration of an invasive component by impedance measurement so as to deliver drug treatments at a precise depth.

In one described embodiment of the present invention, a hollow microneedle is used as a lancet to penetrate the skin for blood sampling. The lancet is also incorporated with one or more penetrating electrodes to detect and measure skin penetration.

Figure 3:
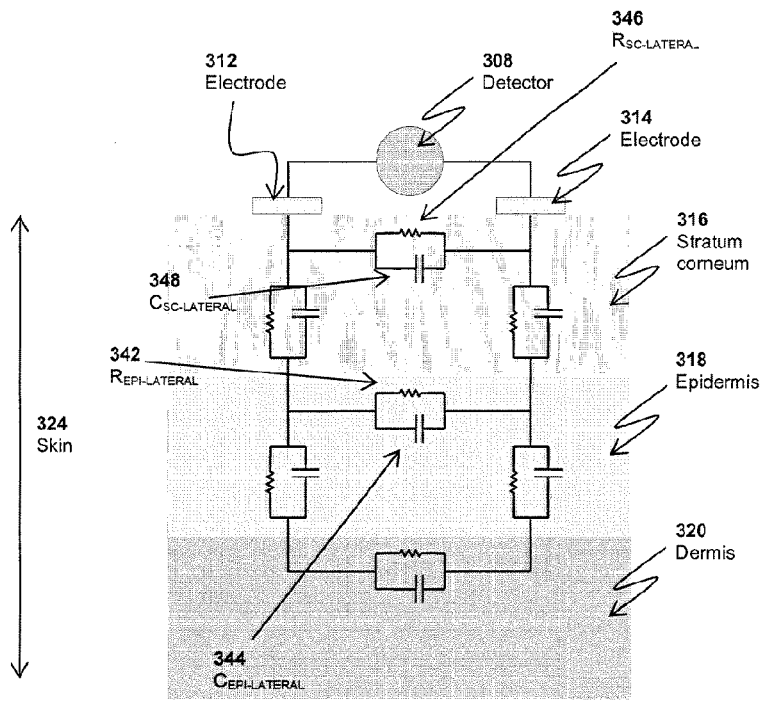
FIG. 3 shows a circuit model representing the skin impedance in accordance to embodiments of the present invention.
Figure 4:
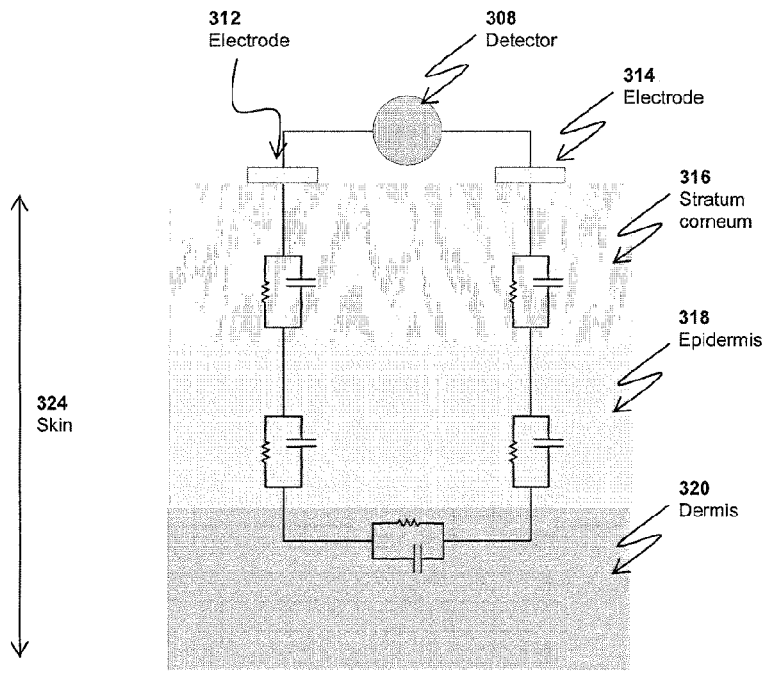
FIG. 4 shows a simplified circuit model representing the skin impedance in accordance to embodiments of the present invention.
Figure 5:
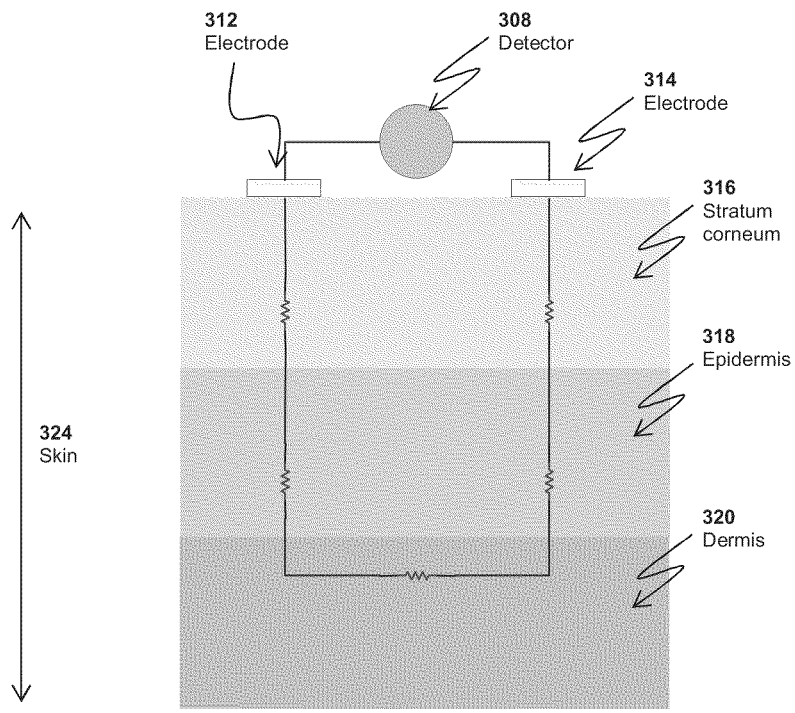
FIG. 5 shows a simplified circuit model representing the skin impedance for DC measurements in accordance to embodiments of the present invention.

A skin impedance model used in the embodiments of the present invention is shown in FIG. 3. The model illustrates the human skin 324 (e.g. the stratum corneum 316, the epidermis 318 and the dermis 320) forming a RC network between electrode 312 and electrode 314. The resistance measured across the electrode 312 and electrode 314 by the detector 308 represents a penetrating resistance $R_{PEN}$. The lateral resistances, $R_{EPI\_LATERAL}$ 342 and $R_{SC\_LATERAL}$ 346 along the epidermis 318 and stratum corneum 316 respectively, is known to be very high as compared with the rest of the resistive and capacitive components in the model. Contrastingly, the capacitance $C_{EPI\_LATERAL}$ 344 and $C_{SC\_LATERAL}$ 348 is known to be comparatively low. Hence, the lateral impedance along the epidermis 318 and stratum corneum 316 respectively, is negligible and is simplified as shown in FIG. 4. In DC measurements, the capacitive components can be disregarded such that the equivalent circuit comprises only of resistive components. This further simplification is shown in FIG. 5.

Figure 6:
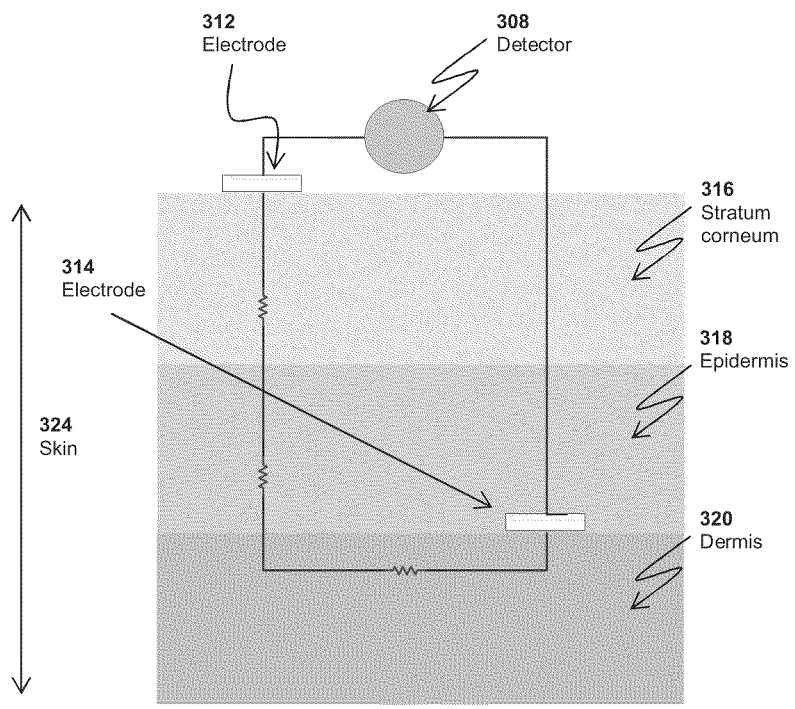
FIG. 6 shows a simplified circuit model representing the skin impedance for DC measurements when an electrode is inserted into the skin in accordance to embodiments of the present invention.

Upon penetrating the skin 324, the invasive component represented by the electrode 314 breaches past the stratum corneum 316 and enters the epidermis 318, but has not yet breached past the epidermis 318. Since the resistance of the stratum corneum 316 is dominant, RPEN reduces significantly. FIG. 6 shows the equivalent circuit when the electrode 314 breaches past the stratum corneum 316 and enters the epidermis 318. The measurement of the penetrating resistance $R_{PEN}$ can be used as an indicator of penetration into the epidermis 318 and dermis 320 from the stratum corneum 316.

Figure 7:
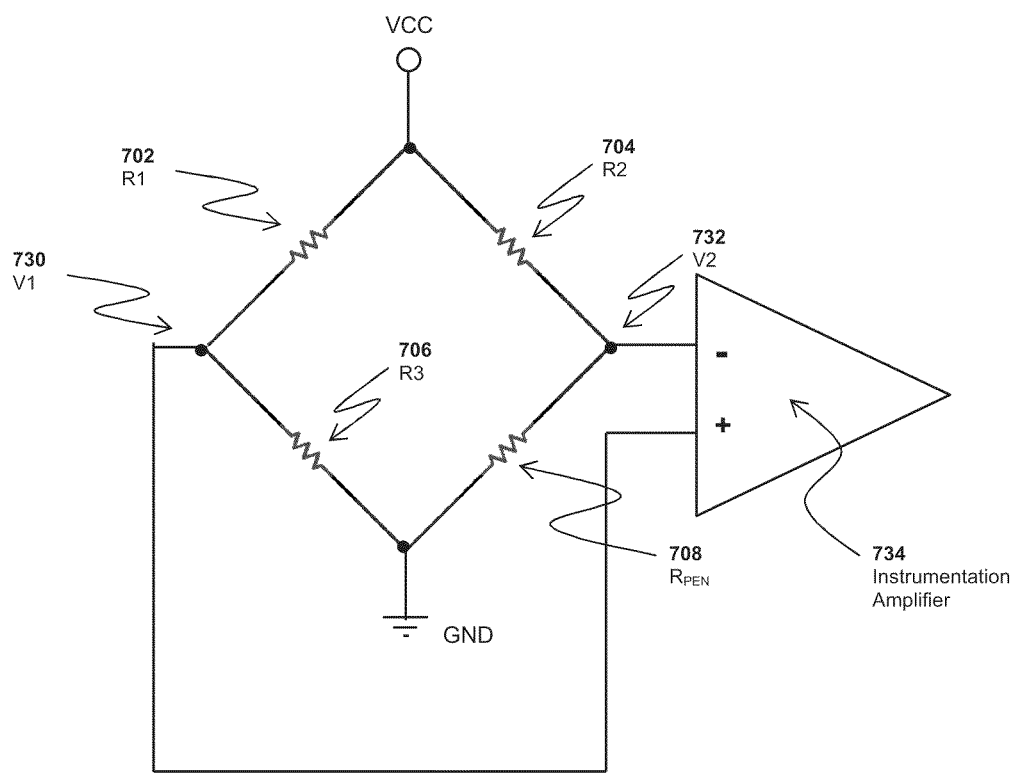
FIG. 7 shows a Wheatstone bridge circuit of the system in accordance to one embodiment of the present invention.

FIG. 7 shows an embodiment of the measurement circuit incorporating a Wheatstone bridge circuit used to measure the penetration. The circuit comprises of three matched reference resistors $R_1$ 702, $R_2$ 704 and $R_3$ 706. The fourth resistance is the penetrating resistance $R_{PEN}$ 708 used to measure the penetration of a penetrating electrode. Consider the case where the reference resistor $R_3$ 706 have matching resistance equal to the penetrating resistance $R_{PEN}$ 708 at zero skin penetration depth, then the voltage potential difference at points $V_1$ 732 and $V_2$ 732 of the bridge circuit is 0 volts. When the penetrating resistance $R_{PEN}$ 708 changes due to skin penetration, the bridge circuit is off-balance and there is now a non-zero voltage potential difference between $V_1$ 730 and $V_2$ 732. It will be appreciated by a person skilled in the art that the potential difference is indicative of skin penetration and this voltage signal can be interfaced to an external circuit for further amplification and processing.

However, if the penetrating resistance $R_{PEN}$ 708 is not zeroised to the value of the reference resistor $R_3$ 706 at zero penetration depth, there is an offset error voltage created by $V_1$ 730 and $V_2$ 732, making the detection of the skin penetration erroneous. Such situations can occur as the skin resistance vary from person to person, site to site and also fluctuate due to environmental and physiological factors. Correcting the offset error voltage and then correlating it against the penetration depth to compensate for the error is impractical as it requires regular calibration effort.

To address the variation in skin resistance in example embodiments, a reference resistance measured at a reference site in close proximity to the penetration site, is used as a "control" during the measurement. Since the reference resistance is preferably taken at a reference site in close proximity to the penetration site, the variation in resistance between the reference resistance and penetration resistance measured is cancelled. The penetration resistance can also be normalised to the reference resistance so that the change is relative instead of absolute. In example embodiments, this can be incorporated into a further modified Wheatstone bridge circuit.

Figure 8:
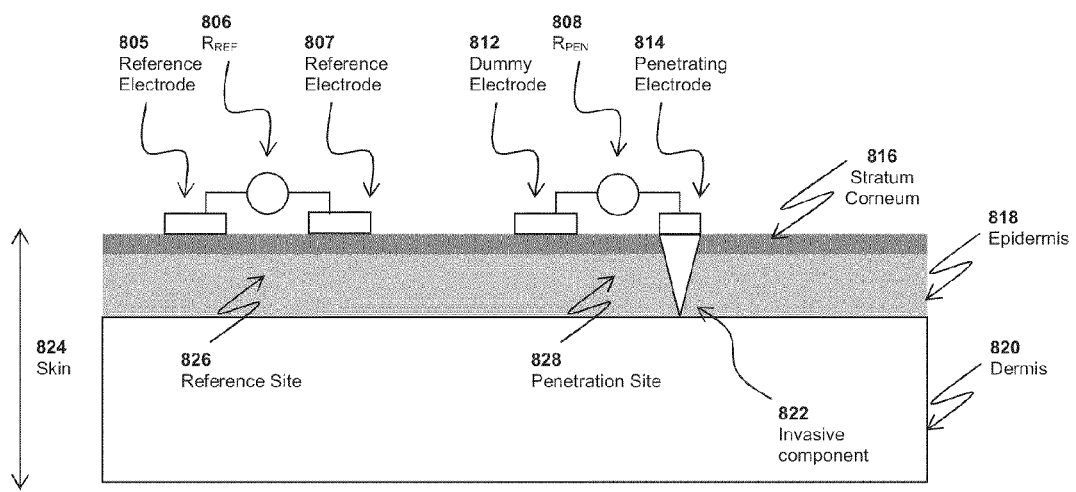
FIG. 8 shows a cross sectional view of the placement of the electrodes in relation to the skin in accordance to one embodiment of the present invention.

FIG. 8 shows an example of how the reference site 826, penetration site 828 and the skin 824 relate to each other. At the penetration site 828, a penetrating resistance $R_{PEN}$ 808 is measured between a dummy electrode 812 and a penetrating electrode 814. In a similar manner at the reference site 826, the reference resistance $R_{REF}$ 806 is measured between the reference electrode 805 and reference electrode 807. While the dummy electrode 812 is usually placed on the skin 824 and the penetrating electrode 814 penetrates into the skin 824 at the penetration site 828 for the purpose of measuring the penetration, the reference electrode 805 and reference electrode 807 are usually placed on the skin at the reference site 826 for sole purpose of measuring the skin reference resistance $R_{REF}$ 806 only. The lateral distance between the reference electrode 805 and reference electrode 807 is preferably equal to the lateral distance between the dummy electrode 812 and penetrating electrode 814.

Figure 9:
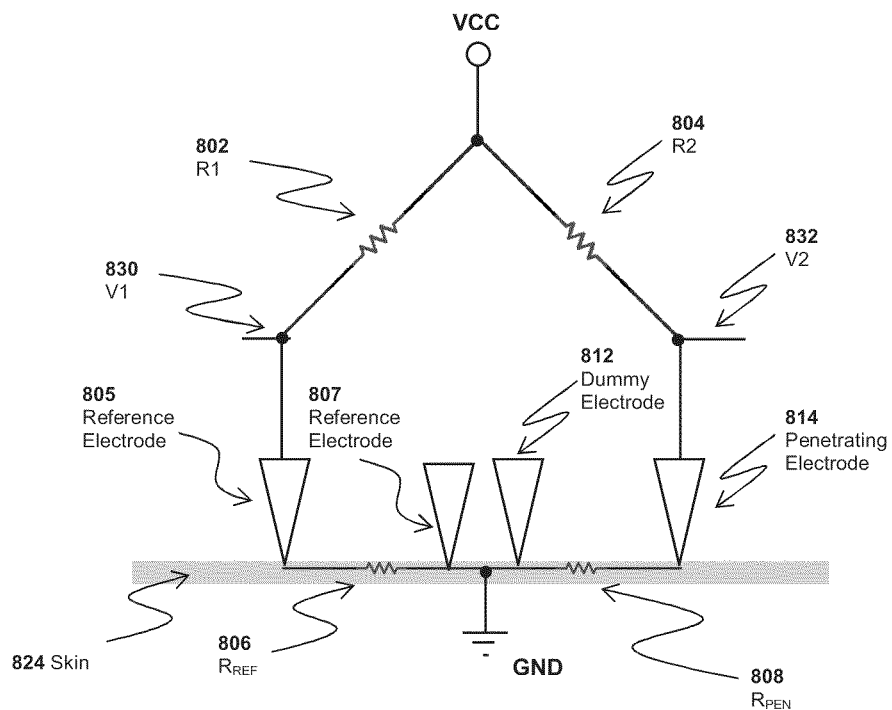
FIG. 9 shows a modified Wheatstone bridge circuit in accordance to one embodiment of the present invention.

FIG. 9 shows how reference resistance $R_{REF}$ 806 is incorporated into the modified Wheatstone bridge circuit in example embodiments. The reference resistance $R_{REF}$ 806 can be used to substitute fixed resistor $R_3$ 808 of FIG. 7. At zero penetration depth, $R_{PEN}$ 808 being measured in close proximity to $R_{REF}$ 806 on the skin 824, is approximately equal to $R_{REF}$ 806 so that the voltage potential difference between $V_1$ 830 and $V_2$ 832 is negligibly 0 volts. Offset error voltage is minimised and the voltage potential difference between $V_1$ 830 and $V_2$ 832 directly indicates skin penetration. This embodiment advantageously solves the variance in skin resistance.

Figure 10:
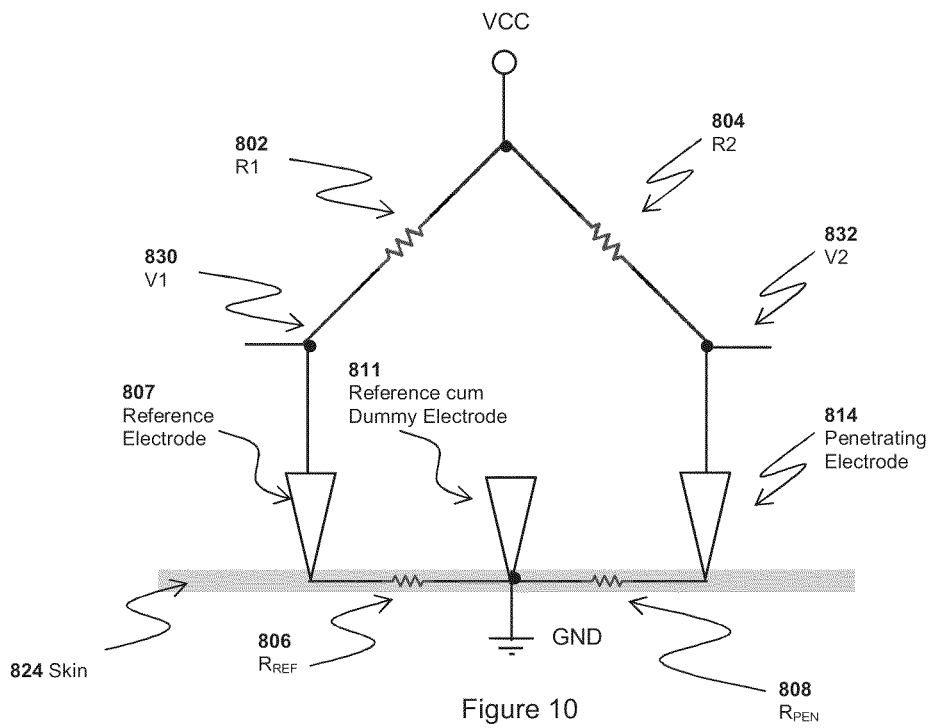
FIG. 10 shows a simplified modification of the Wheatstone bridge circuit in accordance to the embodiment of the invention of FIG. 9.

In a further embodiment of the modified Wheatstone bridge circuit as shown in FIG. 10, the circuit can be further simplified. Since the dummy electrode 812 and the neighbouring reference electrode 807 are at the same voltage potential, both electrodes can be incorporated as one single electrode (i.e. reference cum dummy electrode 811) having the dual function of a dummy electrode 812 and a reference electrode 807.

Figure 11:
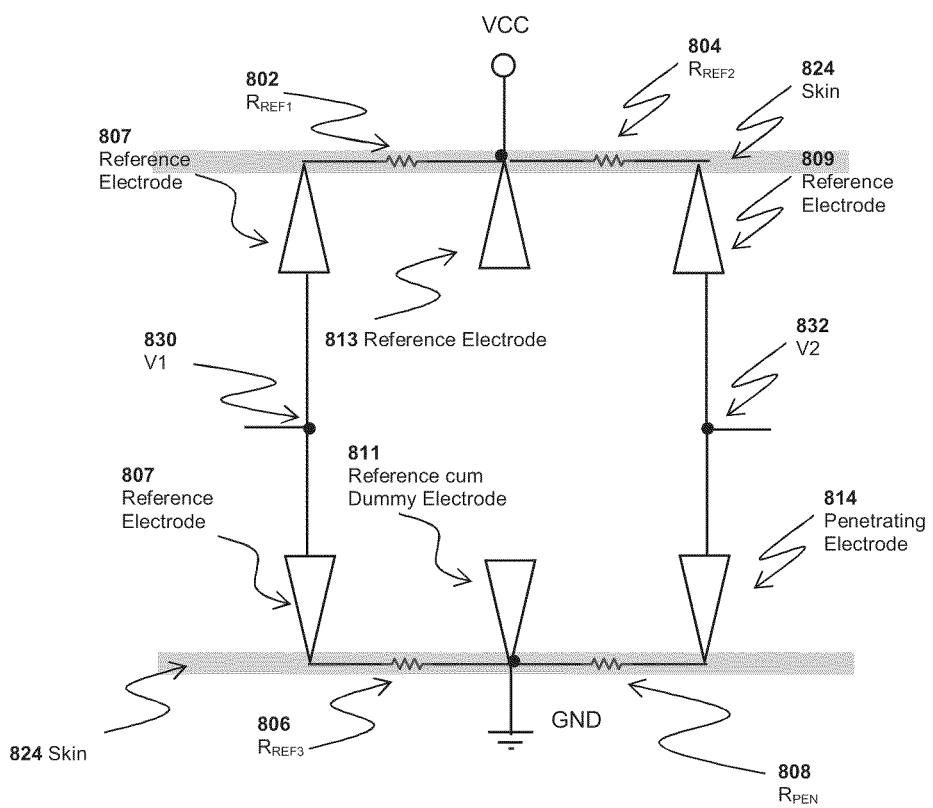
FIG. 11 shows another modified Wheatstone bridge circuit in accordance to one embodiment of the present invention.

In another embodiment as shown in FIG. 11, by employing the cancellation effect of the reference resistance, matched reference resistors $R_1$, $R_2$ and $R_3$ (shown in FIG. 7) are totally replaced with reference resistance $R_{REF1}$ 802, $R_{REF2}$ 804 and $R_{REF3}$ 806 taken at other reference sites in the proximal region of the penetration site. This embodiment eliminates total reliance on stability of the resistance of $R_1$, $R_2$ and $R_3$ but rather on the skin resistance. The reason for this arrangement being that resistance drift in $R_1$, $R_2$ and $R_3$ can also cause erroneous measurements. The selection of reference resistance $R_1$, $R_2$ and $R_3$ are preferably comparable in value to the expected skin resistance so that error drifts in the resistance of $R_1$, $R_2$ and $R_3$ affects the measurements as little as possible. In the worst case scenario, when resistance $R_1$, $R_2$ and $R_3$ are large, even a small percentage drift would affect the measurement by a large amount. By employing reference resistance $R_{REF1}$ 802, $R_{REF2}$ 804 and $R_{REF3}$ 806 taken at other reference sites in the proximal region of the penetration site, the advantage of the cancellation effect is maximised in the embodiment and measurement errors are minimised.

Figure 12:
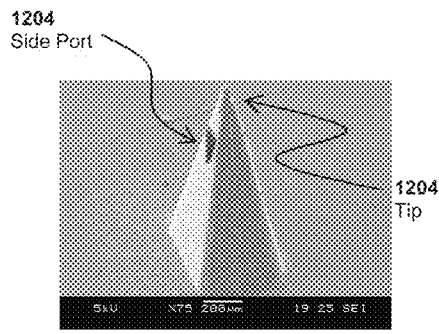
FIG. 12 shows a magnified view of a hollow plastic microneedle in accordance to one embodiment of the present invention.
Figure 13:
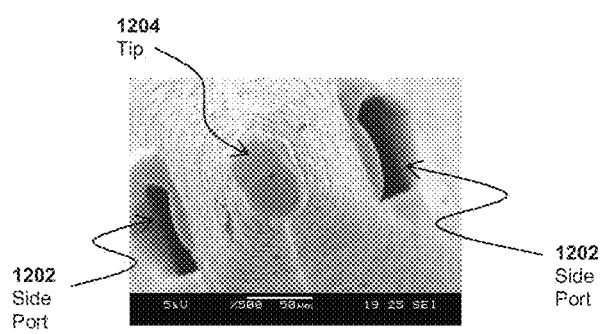
FIG. 13 shows another magnified view of a hollow plastic microneedle in accordance to one embodiment of the present invention.
Figure 14:
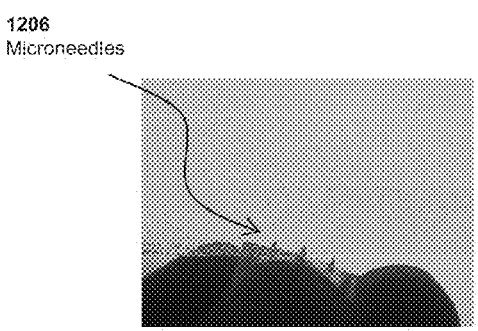
FIG. 14 shows a magnified view of an array of microneedles in accordance to one embodiment of the present invention.

Embodiments of the invasive component can be made of a single microneedle, or an array of microneedles. These microneedles can be solid (without a lumen) or can be hollow (with at least a lumen for transport of fluids). The invasive component can be hollow with delivery holes away from the tip. This allows a sharper tip and reduces the chances of the hole being plugged during the penetration process. A typical side-ported microneedle with a lumen is shown in FIGS. 12, 13 and 14. FIG. 12 shows a magnified view of the tip 1204 and the side port 1202 of a hollow plastic microneedle. A further magnified view in FIG. 13 shows the tip 1204 and two side ports 1202 from another angle of view. FIG. 14 shows an array of three non-conductive (plastic) microneedles 1206.

To be used with the invasive component, a conductive wire is inserted fully into the lumen in such as way that the wire is partially exposed to the outside at the side ports. The exposure of the tip of the wire at the side ports forms the penetrating electrode. The distance between the penetrating electrode and the apex is determined by the distance of the upper edge of side port to the apex. It will be appreciated by a person skilled in the art that the invasive component can have multiple lumens and multiple wires being inserted to form multiple penetrating electrodes for the purpose of measuring skin penetration.

Figure 15:
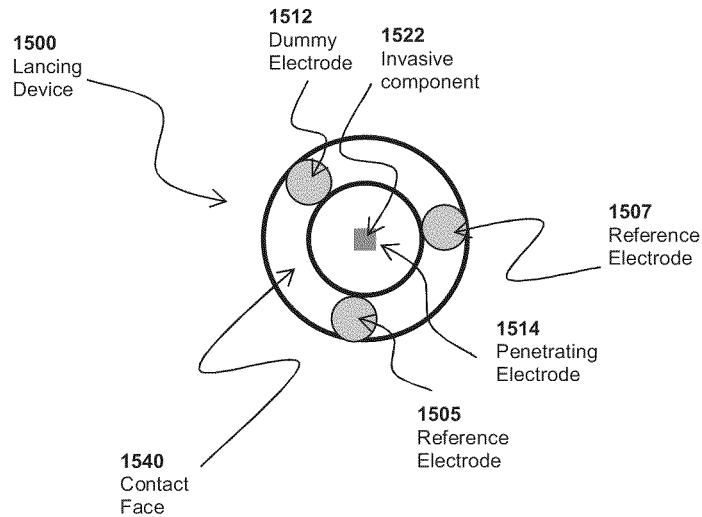
FIG. 15 shows a front view of an invasive component in accordance to one embodiment of the present invention.
Figure 16:
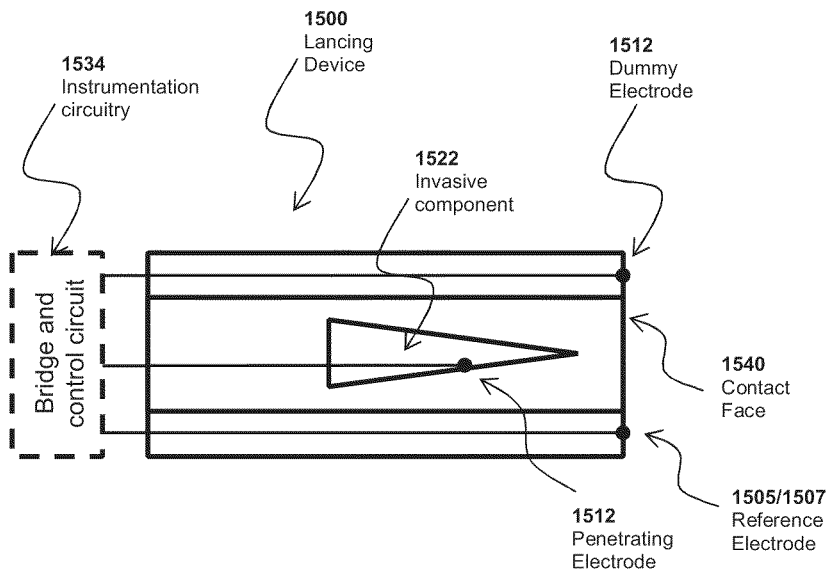
FIG. 16 shows a cross sectional view of the invasive component of FIG. 15 in accordance to one embodiment of the present invention.

A system implementation of the embodiment in FIG. 9 is described now by referring to FIGS. 15 and 16. This implementation incorporates an invasive component 1522 and an instrumentation circuitry 1534 into a lancing device 1500. A penetrating electrode 1514 to penetrate the skin is disposed on the invasive component 1522. Reference electrode 1505, reference electrode 1507 and dummy electrode 1512 are proximally disposed on the contact face 1540 of the lancing device 1500. The reference resistance measured between the reference electrode 1505 and the reference electrode 1507, constitute one leg of the Wheatstone bridge circuit, which is incorporated into the instrumentation circuitry 1534. In a similar manner, the penetrating resistance measured between the dummy electrode 1512 and the penetrating electrode 1514, constitute the mirror leg of the Wheatstone bridge circuit with respect to ground. It will be appreciated by a person skilled in the art that the implementation shown in FIGS. 15 and 16 is not limited to the embodiment shown in FIG. 9, but can be a basis for modification to implement the embodiments shown in FIGS. 10 and 11. For example, the dummy electrode 1512 can be combined with reference electrode 1505 of same voltage potential as shown in FIG. 10. Also, the invasive component 1522 can have multiple penetrating electrodes 1514, form implementation of an embodiment as shown and described below with reference to FIG. 17.

Figure 17:
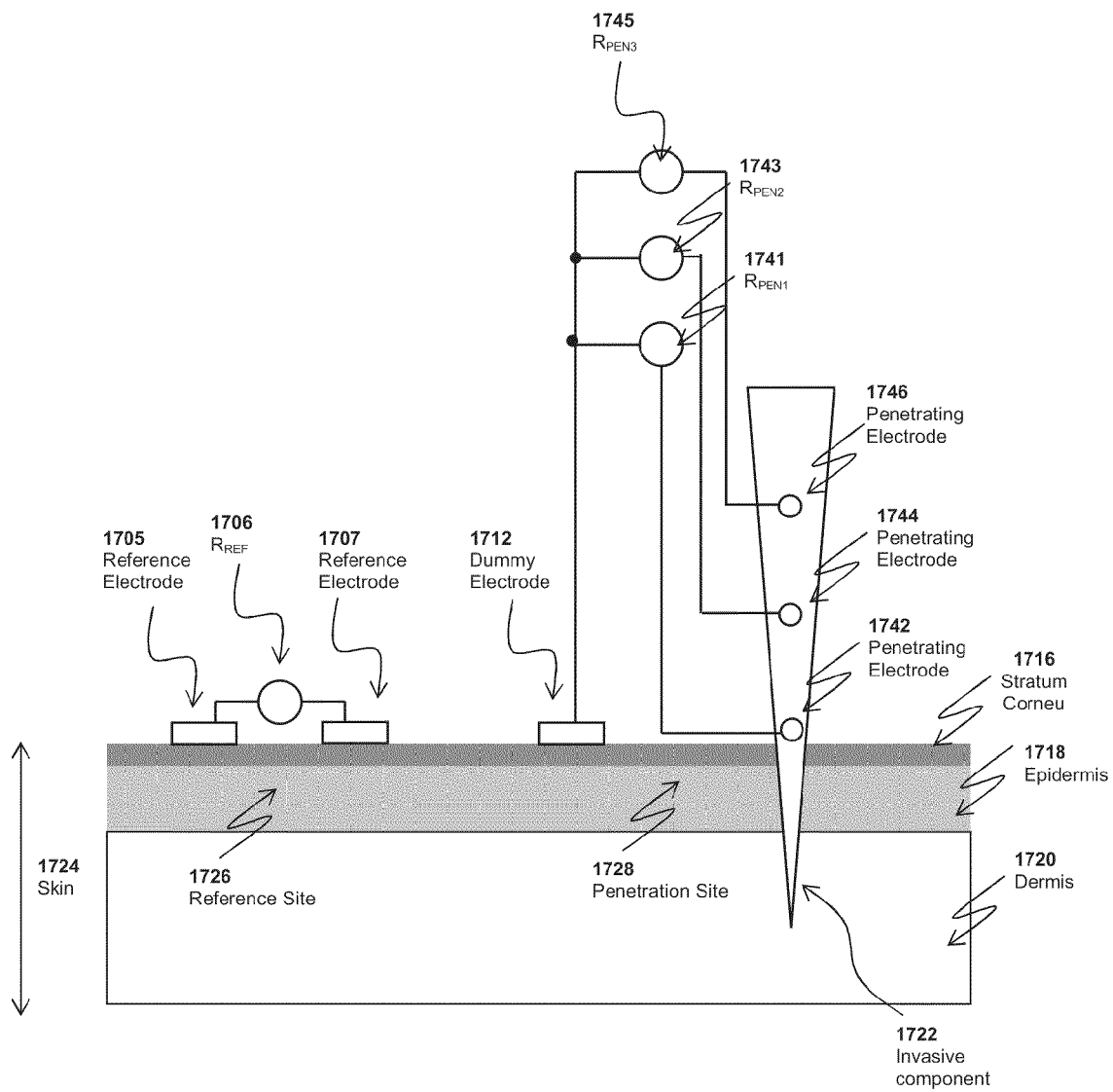
FIG. 17 shows a cross sectional view of the placement of the electrodes in relation to the skin in accordance to one embodiment of the present invention.

The embodiment in FIG. 17 shows how the depth of penetration of an invasive component 1722 can be advantageously and accurately measured. The penetration site 178 is the area where skin penetration is performed. It comprises of a dummy electrode 1712 and one or more conducting penetrating electrodes 1742, 1744 and 1746 on an invasive component 1722. The dummy electrode 1712 is normally placed in contact with skin 1724 at the penetration site 1728 and the penetrating electrodes 1742, 1744 and 1746 are normally disposed on an invasive component 1722, each of which forms an individual resistive loop $R_{PEN1}$ 1741, $R_{PEN2}$ 1743 and $R_{PEN3}$ 1745 with the dummy electrode 1712 at the penetration site 1728. While the penetrating electrodes 1742, 1744 and 1746 are unique to each resistive loop $R_{PEN1}$ 1741, $R_{PEN2}$ 1743 and $R_{PEN3}$ 1745, only one dummy electrode 1712 at the penetration site 1728 is necessary for resistance measurement as the penetrating electrodes 1742, 1744 and 1746 are connected in parallel and terminated at one end at the dummy electrode 1712 and at the other end on the skin 1724 via the invasive component 1722 as shown in FIG. 17. FIG. 17 also shows an example arrangement of the penetrating electrodes 1742, 1744 and 1746 on an invasive component 1722 (e.g. microneedle). The resistive loops $R_{PEN1}$ 1741, $R_{PEN2}$ 1743 and $R_{PEN3}$ 1745 are fed to an external measurement circuit for further processing. Each individual resistive loop $R_{PEN1}$ 1741, $R_{PEN2}$ 1743 and $R_{PEN3}$ 1745 can have a corresponding external unique circuit for resistance measurement. However, it is readily apparent to a person skilled in the art, that multiplexing of resistive loops $R_{PEN1}$ 1741, $R_{PEN2}$ 1743 and $R_{PEN3}$ 1745 to a single external circuit can be incorporated into a single measurement system, minimising component count, circuit layout, etc.

In the embodiment in FIG. 17, when the tip of a penetrating electrode 1742, 1744 and 1746 has reached the epidermis 1718 beyond the stratum corneum 1717, the resistive loop $R_{PEN1}$ 1741, $R_{PEN2}$ 1743 and $R_{PEN3}$ 1745 drops from an immeasurable resistance figure (e.g. infinity) to a measurable figure. This property of the reduction in measurable resistance figure of the resistive loop $R_{PEN1}$ 1741, $R_{PEN2}$ 1743 and $R_{PEN3}$ 1745 indicates penetration of the respective penetrating electrode 1742, 1744 and 1746 into the epidermis 1718. If the penetrating electrodes 1742, 1744 and 1746 are placed at predetermined distance from each other, penetration depth of the invasive component 1722 can be determined by detecting which resistive loops $R_{PEN1}$ 1741, $R_{PEN2}$ 1743 and $R_{PEN3}$ 1745 experience a reduction in measurable resistance figure. It is readily apparent to a person skilled in the art that the detection of the reduction in measurable resistance figure can be incorporated onto the instrumentation circuitry. It is also apparent that the invasive component 1722 in such an embodiment is preferably non-conductive in order to readily incorporate multiple penetrating electrodes 1742, 1744 and 1746. On the other hand, for a single penetrating electrode 1742, the invasive component can be either conductive or non-conductive.

In another embodiment, a display device indicating skin penetration depth can also be incorporated into the instrumentation circuitry using inorganic/organic light emitting diode (LED) or a liquid crystal device (LCD) based display panel. The indication of skin penetration and its depth is useful as the user is often obscured from viewing the penetration site. Such indication allows the user to be informed of the penetration outcome without taking the lancing device away from the penetration site.

It will be appreciated by one skilled in the art in the implementation of the instrumentation circuitry, that there can be instances where the resistance change may be detected, but where the resistance change does not validly show the penetrating electrode penetrating the skin. The instrumentation circuitry in the example embodiments is designed to avoid such incorrect indications. This is described with reference to modifications to the embodiments in FIGS. 7, 9, 15 and 16, and where V1 830 and V2 832 are connected to the instrumentation amplifier 734 at the positive and negative inputs respectively. The instrumentation amplifier 734 is designed such that it only produces a voltage output when there is a positive voltage difference between the positive and negative inputs respectively.

Before the lancing device 1500 is in contact with the skin, none of the electrodes are in contact with the skin 824. Thus, the reference resistance $R_{REF}$ 806 is at an infinite value. Similarly, the penetrating resistance $R_{PEN}$ 808 at that stage is also at an infinite value. There is no imbalance in the bridge circuit due to the equality of the differential voltages of V1 830 and V2 832, as both $R_{REF}$ 806 and $R_{PEN}$ 808 are infinitely large. The voltage output at the instrumentation amplifier 734 with respect to ground, would be approximately zero.

When the lancing device 1500 just makes contact with the skin 824, all of the electrodes except the penetrating electrode 1514 (i.e. reference electrodes 1505/1507 and dummy electrodes 1512 only) make contact with the skin 824. The reference resistance $R_{REF}$ 806 is now measurable between reference electrode 1505 and reference electrode 1507. In contrast, the penetrating resistance $R_{PEN}$ 808 remains unchanged. Thus, there is a voltage imbalance in the bridge circuit due to the differential voltages, but because V1 830 and V2 832 would produce a negative voltage difference there would not be any voltage output at the instrumentation amplifier 734.

When the penetrating electrode 1514 disposed in the invasive component 1522, just makes contact with the skin 824, the penetrating resistance $R_{PEN}$ 808 is reduced to a resistance equal to the reference resistance $R_{REF}$ 806. The equality of the penetrating resistance $R_{PEN}$ 808 and reference resistance $R_{REF}$ 806, swings the bridge circuit back into balance. Thus, the voltage output of the instrumentation amplifier 734 with respect to ground, would swing back to zero.

When the penetrating electrode 1514 disposed in the invasive component 1522 further invades into the skin 824, the penetrating resistance $R_{PEN}$ 808 is further reduced in resistance than the reference resistance $R_{REF}$ 806, as it further invades the layers of the skin 824, thus producing a positive voltage difference between the positive and negative inputs of the instrumentation amplifier 734 respectively. The voltage output of the instrumentation amplifier 734 with respect to ground, would swing to a positive value as a result, indicative of "true" skin penetration.

It will also be appreciated by a person skilled in the art that the discussion described above is not limited to the embodiments shown in FIGS. 7, 9, 15 and 16, but is applicable to the implementation of the other embodiments discussed herein.

Figure 18:
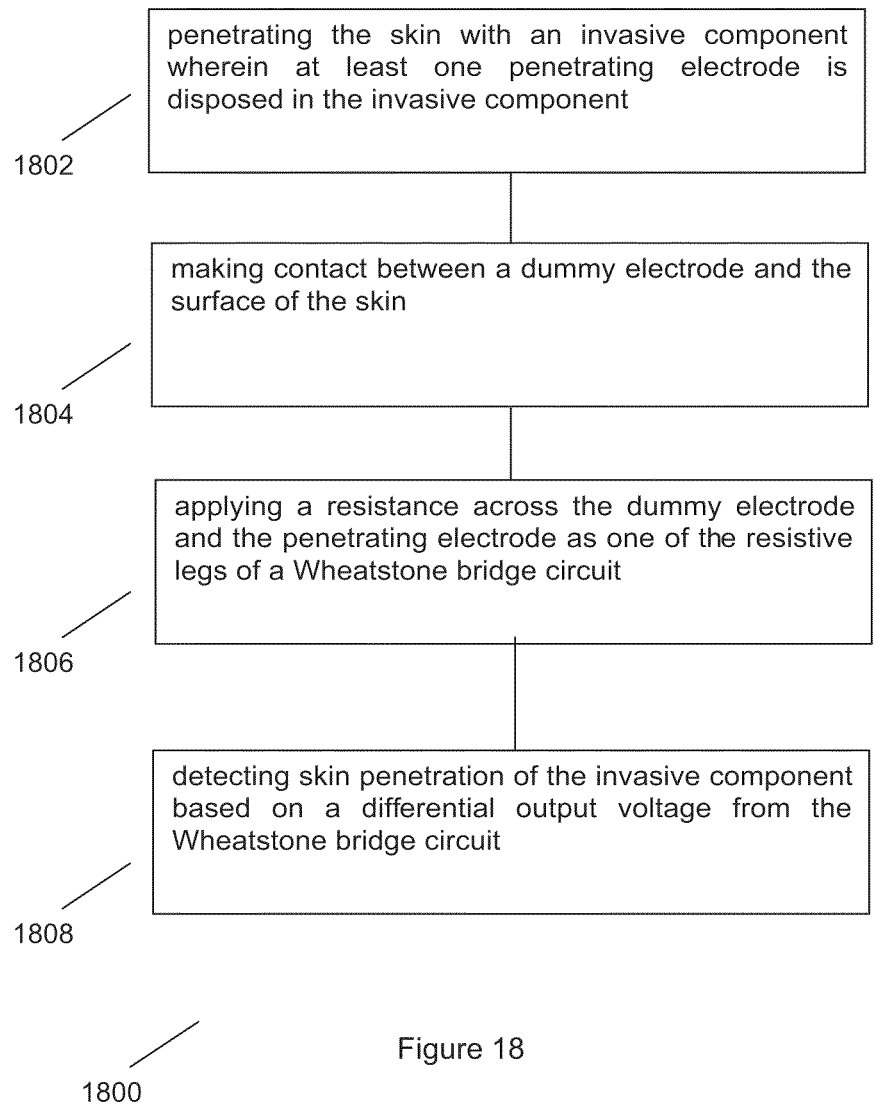
FIG. 18 shows a flow chart illustrating a method for detecting skin penetration according to an example embodiment.

FIG. 18 shows a flow chart 1800 illustrating a method for detecting skin penetration according to an example embodiment. At step 1802, the skin is penetrated with an invasive component wherein at least one penetrating electrode is disposed in the invasive component. At step 1804, contact is made between a dummy electrode and the surface of the skin. At step 1806, a resistance is applied across the dummy electrode and the penetrating electrode as one of the resistive legs of a Wheatstone bridge circuit. At step 1808, skin penetration of the invasive component is detected based on a differential output voltage from the Wheatstone bridge circuit.

Embodiments of the present invention aim to detect the change in skin property during the skin penetration by an invasive component such as a microneedle or lancet. In addition, some of the embodiments mentioned can be readily and advantageously incorporated into polymer lancets.

The electrical properties such as the impedance, the capacitance or the electrical resistance between two electrodes on the skin are different compared to that when one of the electrodes is inserted in the skin. By incorporating a measurement circuit, the relative change in electrical property, such as the electrical resistance, can be measured. Relative change instead of absolute change is measured as the absolute values of skin impedance vary according to the bodily, environmental and physiological factors. This allows the embodiments to be used on any body without overwhelming calibration and correlation.

To more accurately control the penetration depth, e.g., various penetrating electrodes are placed at predetermined positions along the invasive component's tip, forming points of measurement in one embodiment. The detection of change in value signifies that a particular electrode has made contact with respective layers of the inner skin, thereby providing depth of penetration of the invasive component.

By making use of detection circuitry, the embodiments can provide various means of controlling the insertion actuation, thereby providing an accurate and reliable means to determine the depth of skin penetration. Combined with other instrumentation, readouts can be displayed and preferably make the usage more intuitive.

The proposed system can combine the various embodiments described and incorporate into a single lancing device, enabling an integrated one-step blood testing device. For example, a lancing device with features to automate skin penetration depth while displaying skin penetration/depth on the display LCD/LED and onboard blood sampling/analysis test circuitry after collection of the blood samples. The lancing device can also deliver a precise amount of drug to a defined skin depth and display the delivery progress.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

We claim:

1. A system for detecting skin penetration, the system comprising:
   an invasive component for penetrating the skin;
   a dummy electrode for making contact with the surface of the skin;
   at least one penetrating electrode disposed in the invasive component;
   a Wheatstone bridge circuit;
   wherein a resistance across the dummy electrode and the penetrating electrode constitutes one of the resistive legs of the Wheatstone bridge circuit, and
   a first pair of reference electrodes for making contact with the surface of the skin, wherein a skin resistance across the first pair of reference electrodes constitutes the mirroring resistive leg, with respect to ground, of the Wheatstone bridge circuit;
   wherein the system is configured to detect a depth of skin penetration of the invasive component based on a differential output voltage from the Wheatstone bridge circuit.

2. The system as claimed in claim 1, wherein one of the reference electrodes is the dummy electrode.

3. The system as claimed in claim 1, further comprising second and third pairs of reference electrodes, each for making contact with the surface of the skin, wherein respective skin resistances across the second and third pairs of reference electrodes constitute the remaining resistive legs of the Wheatstone bridge circuit respectively.

4. The system as claimed in claim 1, wherein a plurality of penetrating electrodes are disposed in the invasive component.

5. The system as claimed in claim 4, wherein resistances across the dummy electrode and the respective penetrating electrodes are multiplexed across one of the resistive legs of the Wheatstone bridge circuit connected to the respective penetrating electrodes, and the depth of skin penetration of the invasive component is detected based on differential output voltages from the Wheatstone bridge circuit induced by the respective resistances across the dummy electrode and the respective penetrating electrodes.

6. The system as claimed in claim 1, wherein the invasive component comprises a microneedle disposed in a lancing device, and the dummy electrode for making contact with the surface of the skin is disposed on a skin-contact face of the lancing device.

7. The system as claimed in claim 1, wherein the invasive component comprises a microneedle disposed in a lancing device, and the dummy electrode for making contact with the surface of the skin and the first pair of reference electrodes are disposed on a skin-contact face of the lancing device.

8. The system as claimed in claim 3, wherein the invasive component comprises a microneedle disposed in a lancing device, and the dummy electrode for making contact with the surface of the skin and the first, second, and third pairs of reference electrodes are disposed on a skin-contact face of the lancing device.

9. The system as claimed in claim 1, wherein the invasive component comprises a hollow or solid microneedle.

10. The system as claimed in claim 1, wherein the invasive component comprises a conductive microneedle.

11. The system as claimed in claim 1, wherein the invasive component comprises a non-conductive microneedle.

12. The system as claimed in claim 11, wherein the invasive component comprises a plastic microneedle.

13. The system as claimed in claim 1, further comprising means for indicating the depth of skin penetration of the invasive component based on the differential output voltage from the Wheatstone bridge circuit.

14. The system as claimed in claim 1, further comprising means for displaying the depth of skin penetration of the invasive component based on the differential output voltages from the Wheatstone bridge circuit.

15. The system as claimed in claim 6, wherein the reference and/or dummy electrodes are disposed around an opening of a distal end of the lancing device.

16. A method for detecting skin penetration, the method comprising the steps of:
   penetrating the skin with an invasive component wherein at least one penetrating electrode is disposed in the invasive component;
   making contact between a dummy electrode and the surface of the skin;
   applying a resistance across the dummy electrode and the penetrating electrode as one of the resistive legs of a Wheatstone bridge circuit;
   making contact with the surface of the skin with a first pair of reference electrodes;
   applying a skin resistance across the first pair of reference electrodes as the mirroring resistive leg, with respect to ground, of the Wheatstone bridge circuit; and
   detecting a depth of skin penetration of the invasive component based on a differential output voltage from the Wheatstone bridge circuit.

17. The method as claimed in claim 16, wherein one of the reference electrodes is the dummy electrode.

18. The method as claimed in claim 16, further comprising the steps of:
   making contact with the surface of the skin with second and third pairs of reference electrodes, and
   applying respective skin resistances across the second and third pairs of reference electrodes as the remaining resistive legs of the Wheatstone bridge circuit respectively.

19. The method as claimed in claim 16, wherein a plurality of penetrating electrodes are disposed in the invasive component.

20. The method as claimed in claim 19, wherein resistances across the dummy electrode and the respective penetrating electrodes are multiplexed to one of the resistive legs of the Wheatstone bridge circuit connected to the respective penetration electrodes and the depth of skin penetration of the invasive component is detected based on differential output voltages from the Wheatstone bridge circuit induced by the respective resistances across the dummy electrode and the respective penetrating electrodes.

21. The method as claimed in claim 16, wherein the invasive component comprises a microneedle disposed in a lancing device, and the dummy electrode for making contact with the surface of the skin is disposed on a skin-contact face of the lancing device.

22. The method as claimed in claim 16, wherein the invasive component comprises a microneedle disposed in a lancing device, and the dummy electrode for making contact with the surface of the skin and the first pair of reference electrodes are disposed on a skin-contact face of the lancing device.

23. The method as claimed in claim 18, wherein the invasive component comprises a microneedle disposed in a lancing device, and the dummy electrode for making contact with the surface of the skin and the first, second, and third pairs of reference electrodes are disposed on a skin-contact face of the lancing device.

24. The method as claimed in claim 16, wherein the invasive component comprises a hollow or solid microneedle.

25. The method as claimed in claim 16, wherein the invasive component comprises a conductive microneedle.

26. The method as claimed in claim 16, wherein the invasive component comprises a non-conductive microneedle.

27. The method as claimed in claim 26, wherein the invasive component comprises a plastic microneedle.

28. The method as claimed in claim 16, further comprising the step of:
   indicating the depth of skin penetration of the invasive component based on the differential output voltage from the Wheatstone bridge circuit.

29. The method as claimed in claim 20, further comprising the step of:
   displaying the depth of skin penetration of the invasive component based on the differential output voltages from the Wheatstone bridge circuit.

* * * * *